United States Patent [19]

Hsiao et al.

[11] Patent Number: 4,803,079

[45] Date of Patent: *Feb. 7, 1989

[54] CONTROLLED RELEASE NAPROXEN AND NAPROXEN SODIUM TABLETS

[75] Inventors: Charles H. Hsiao, Cooper City, Fla.; John S. Kent, Palo Alto, Calif.

[73] Assignee: Syntex (U.S.A.) Inc., Palo Alto, Calif.

[*] Notice: The portion of the term of this patent subsequent to Feb. 18, 2003 has been disclaimed.

[21] Appl. No.: 811,575

[22] Filed: Dec. 20, 1985

Related U.S. Application Data

[63] Continuation-in-part of Ser. No. 504,112, Jun. 14, 1983, Pat. No. 4,571,333.

[51] Int. Cl.[4] .......................... A61K 9/22; A61K 9/26
[52] U.S. Cl. ...................................... 424/468; 424/465; 424/462; 424/470; 424/476; 424/480; 424/488; 514/570; 514/781
[58] Field of Search .................... 424/19-22, 424/35, 465, 469, 470, 468, 476, 480, 488; 514/570, 781

[56] References Cited

U.S. PATENT DOCUMENTS

| | | | |
|---|---|---|---|
| 3,065,143 | 11/1962 | Christensen et al. | 424/19 |
| 3,424,842 | 1/1969 | Nurnberg | 424/19 |
| 3,870,790 | 3/1975 | Lowey et al. | 424/19 |
| 4,226,849 | 10/1980 | Schor | 424/19 |
| 4,369,172 | 1/1983 | Schor et al. | 424/19 |
| 4,571,333 | 2/1986 | Hsiao et al. | 424/22 |

OTHER PUBLICATIONS

Borzunov, E., *Farmatsevtichinii Zhurnal*, Kiev, vol. 25(5) 1970, pp. 76-77.

Davis, S. S. et al., "Scintigraphic Studies on the In Vivo Dissolution of a Buccal Tablet", Modern Concepts in Nitrate Delivery Systems, Ed. by A. A. J. Goldberg and D. J. Parsons, 1983: Royal Society of Medicine International Congress and Symposium Series No. 54, pp. 30-37.

Kassem, A. A., "Enhancement of Release Rate of Spirolactone from Tablets by Formation of Solid Dipersions with Water-Soluble Polymer", *Bull etin of the Faculty of Pharmacy*, Cairo University, vol. 10(1) 1980, pp. 275-307.

Gudsoorkar, V. R., and Khanna, S., "Influence of Binders on Some Physical Parameters of Lactose and Sulfadimidine Tablets", Indian Drugs and Pharmaceuticals Industry, vol. 15(4), 1980, pp. 3-5.

Korsmeyer, R. W. et al., "Mechanisms of Potassium Chloride Release for Compressed, Hydrophilic, Polymeric Matrices: Effect of Entrapped Air", *Journal of Pharmaceutical Science*, vol. 72(10) 1983, pp. 1189-1191.

Koycer, I. and Pope, D. G., "An Evaluation of Tablet Binding Agents, Part II, Pressure Binger", *Powder Technology*, vol. 34(1) 1983, pp. 53-56.

Ibid, pp. 39-51.

Laguna, O. et al., "Enrobage.-III, Influence de quelques produits filmogenes at plastifiants sur la dissolution de comprimes a base de chlorure de sodium", *Annales Pharmaceutiques Francaise*, 1975, vol. 33(5) pp. 235-242.

Lapidus, H., "Drug Release from Compressed Hydrophilic Matrices", (Abstract) Order 67-14, 728 from Chemistry, pp. 2363-2364-B.

Malkowska, S. et al., "Effect of Re-Compression on the Properties of Tablets Prepared by Moist Granulation", (List continued on next page.)

*Primary Examiner*—Shep K. Rose
*Attorney, Agent, or Firm*—Ellen J. Wise; Tom M. Moran; Alan M. Krubiner

[57] ABSTRACT

A controlled release tablet for once-daily oral administration of about 500-1200 mg of naproxen or naproxen sodium, said tablet comprising a homogeneous matrix comprising about 4-9 weight percent of hydroxypropyl methylcellulose having a number average molecular weight in the range of from about 80,000 to about 130,000, about 81-96 weight percent naproxen or naproxen sodium, and 0.1 to about 2 weight percent of a pharmaceutically acceptable lubricating agent, and optionally including a pharmaceutically acceptable coating.

17 Claims, 3 Drawing Sheets

OTHER PUBLICATIONS

Drug Development and Industrial Pharmacy, 9(3), pp. 349–361 (1983).

Miseta, M. "Influence of Pressing Force on the Physical Features of Sulfathiazole Tables and on the Dissolution Rate of Active Ingredient", Pharmazie, vol. 38(5), 1983, pp. 326–327.

Misetta, M. "die Beziehung zwischen Preskraft und Rollfestigkeit bei Sulfathidol-Tabletten", Pharmazie, vol. 38(8), 1983, pp. 567.

Nagy, G. et al., "Untersuchyngen uber die Txtur und die Eigenschaften von Acetyl-Salicylsaure-Tabletten", Pharmazie, vol. 33(11), 1978, pp. 747–749.

Pintye-Hodi, K. et al., "Untersuchugen unber die Txtur und die Eigenschaften von Acetyl-Salicylsaure-Tablet- ten", Pharmazie, vol. 35(3), 1980, pp. 168–70.

Solomon, J. L. et al., "Sustained Release of a Water Soluble Drug from Hydrophilic Compressed Dosage Forms" Pharm. Ind., vol. 41(8), 1979, pp. 799–802.

*Formulating Sustained Release Pharmaceutical with Methocel and Insoluble Fillers; Product Information for Methocel,* published by Dow Chemical Co, 1982.

Lapidus, H., Drug Release from Compressed Hydrophillic Matrices (Ann Arbor, Mich.: University Microfilms, Catalog Entry 67–14,728 (1969) (Lapidus Thesis).

Lapidus, H. and Lordi, N. G., N. G., *J. Pharm Sci.,* vol. 55, No. 8, 840–843.

Lapidus, H., and Lordi, N. G., *J. Pharm. Sci.,* vol. 57, No. 8, 1292–1301.

Salomon et al., *Pharm. Acta. Hevl.,* vol. 54, No. 3, pp. 82–85 (1979).

CONTROLLED RELEASE NAPROXEN AND NAPROXEN SODIUM TABLETS

This is a continuation-in-part of application Ser. No. 504,112 filed June 14, 1983, now U.S. Pat. No. 4,571,333.

BACKGROUND OF THE INVENTION

1. Field of the Invention.

The present invention relates to controlled release preparations of (+)-6-methoxy-alpha-methyl-2-naphthaleneacetic acid (naproxen) and its pharmaceutically acceptable sodium salt (naproxen sodium). Specifically it relates to an oral dosage form comprising a matrix of naproxen or naproxen sodium in high molecular weight hydroxypropyl methylcellulose, which provides a release period suitable for daily dosing and exhibits good bioavailability.

2. Description of Related Art.

Naproxen and naproxen sodium are well known and widely used anti-inflammatory medications with analgesic and antipyretic properties. They are used for the relief of pain and inflammation generally, and for specific conditions such as arthritis and dysmenorrhea. Naproxen is available in 250 mg, 375 mg and 500 mg tablets and is generally administered in therapeutic doses of 500–1000 mg per day with dosing intervals of 8–12 hours. Naproxen sodium is available in 275 mg tablets and is generally administered in therapeutic doses of 550–1100 mg per day with dosing intervals of 8–12 hours.

Hydroxypropyl methylcelluloses are commercially available in various grades, under several tradenames, including Methocel E, F, J and K (all previously designated as Methocel HG) from The Dow Chemical Co., U.S.A., HPM from British Celanese, Ltd., England, and Metolose SH from Shin-Etsu, Ltd., Japan. The various grades available under a given tradename represent differences in methoxy and hydroxypropoxyl content as well as molecular weight and viscosity. Commercial designations of the various hydroxypropylmethylcellulose reflect their individual viscosity types and are based on the viscosities of 2% aqueous solutions at 20° C. as determined according to the method described in the *United States Pharmocopeia*, Rev. 20. The viscosities range from 15 cps to 100,000 cps and represent number average molecular weights of from about 10,000 to over 150,000. In general, each of the various grades under a given tradename is a hydroxypropyl methylcellulose of a single viscosity type, e.g. 50 cps, 100 cps, 4000 cps, 15,000 cps, etc.

The area of controlled release pharmaceuticals is increasingly important in the formulation, manufacture and marketing of new pharmaceutical products. The technologies and corresponding products of this art are variously described as, among others, sustained release, controlled release, prolonged action, depot, repository, delayed action, retarded release, and timed release pharmaceuticals. In describing the present invention, the term "controlled release" is used to indicate that control is exercised over both the duration and profile of the in vivo drug release curve.

Controlled release drug dosage forms offer many advantages over conventional dosage forms for particular drugs. Of major importance both practically and therapeutically is the decrease in frequency of administration required to achieve the desired effect. A dosage form which is taken only once-a-day greatly improves patient compliance, and by extending the drug's activity through the night, permits the patient to sleep undisturbed until the morning. By enhancing the acceptability of a medication regime, patient compliance, and hence therapy, is improved.

Another important therapeutic advantage of some controlled release drug dosage forms is a reduction in the fluctuation of plasma drug concentrations. The pharmacologic basis for minimizing fluctuations in plasma drug levels derives from three basic principals. First, every drug has a therapeutic blood level that must be reached if the desired benefit is to be achieved from its use. When the condition being treated requires multiple doses over an extended period of time, the therapeutic blood level is the drug level which must be maintained to maximize the effectiveness of the medication. Second, most drugs have toxic blood levels that define the limit above which adverse reactions, or side effects, are experienced. Third, the drug concentration-response curve for most drugs is such that activity is approximately proportional to the logarithm of concentration. From these pharmacologic principles, a rationale for closely maintained plasma drug levels can be inferred. Several years of clinical testing has supported that rationale, and it is now widely agreed that where continuous drug treatment is desirable, therapy is optimized when the plasma drug concentration is maintained near the therapeutic level.

The mode of drug administration can influence the time course of therapeutic activity by affecting the profile of drug concentration in the blood. Conventional drug dosage forms are rapidly absorbed into the circulation and then metabolized; the blood level profile of the drug following a single conventional dose typically is defined by an initial high peak, followed by a rapid decline, the slope and duration of which depends upon such factors as the half-life of the drug. The initial high peak typically substantially exceeds the therapeutic plasma concentration range, and represents a large portion of the drug contained in the dosage form. After multiple periodic doses, a steady state mean plasma drug concentration is achieved, but the absolute level fluctuates in peaks and troughs above and below the mean level.

In contrast, controlled release drug dosage forms can extend the duration of therapeutic drug levels in the blood, and minimize or even avoid the initial spike in blood level concentration which is typical of conventional dosage forms. Additionally, while controlled release oral dosage forms do not inherently reduce the fluctuations in plasma drug concentrations, an opportunity to minimize these fluctuations arises from the fact that the rate of drug release is metered over a prolonged period of time.

A decrease in the fluctuation of plasma drug levels is achieved by balancing the in vivo release rate against the pharmacokinetics of the drug, i.e. absorption, distribution, metabolism and exretion, so that plasma drug level variation is minimized. The time course of change of drug concentration in the blood is the net result of the rate of delivery into, and the pharmacokinetic behavior of the drug in, the body.

Conventional dosage forms of naproxen and naproxen sodium are administered two to three times daily in order to maintain therapeutic blood levels, and to minimize the differential between peak and through blood levels during multiple dose therapeutic regimens. Peak to trough blood level ratios of about 2:1 are generally achieved with these regimens. In the interest of maximizing the therapeutic effectiveness of the drug, it is desirable to minimize as much as possible the ratio of peak to trough blood levels obtained during multiple dose therapy. Controlled release formulations generally permit less frequent dosing intervals to obtain acceptable peak to trough blood level ratios.

Many different types of controlled release oral dosage forms have been developed, but each has disadvantages which affect its suitability to a particular drug and therapeutic objective. Wide variations in the physicochemical and pharmacokinetic properties of different drugs impose such varied requirements on the design of controlled drug delivery formulations, that formulations which are suitable for one drug cannot generally be predictably applied to other drugs. A formulation which incorporates the drug in a soluble or erodible matrix is desirable due to its ease of manufacture, low incidence of lot to lot variability, and relatively low cost. The use of hydrophilic gums such as hydroxypropyl methylcellulose as sustained release matrix materials is known and has been demonstrated with a variety of active agents. However, no formulation of this type is known which is well suited for the controlled release of either naproxen or naproxen sodium.

Christenson and Dale (U.S. Pat. No. 3,065,143) disclosed the use of certain hydrophilic gums, including hydroxypropyl methylcellulose, as carrier base materials in the preparation of sustained release pharmaceutical tablets. The tablets consisted essentially of a mixture of a drug in combination with at least one-third part by weight of the hydrophilic gum. Examples 1 and 7 disclose the use of Methocel 60HG 4,000 cps (now known as Methocel E4M) which has a number average molecular weight of 93,000, as calculated from the data in the "Handbook of Methocel Cellulose Ether Products" (The Dow Chemical Co., 1974). Example 4 discloses the use of Methocel 90HG 4,000 cps, and Example 5 discloses the use of Methocel 90HG 15,000 cps, (now known as Methocel E4M and K15M respectively). The 4,000 cps and 15,000 cps viscosity grades indicate that the polymers have number average molecular weights of 89,000 and 124,000, respectively. Polymer to drug ratios given in the examples range from 1:2 to 10:1 and durations of sustained released of up to 12 hours in vitro are disclosed.

Schor and Nigalaye (U.S. Pat. No. 4,369,172, 1983) have disclosed the use of certain hydroxypropylmethylcelluloses for "prolonged release therapeutic compositions." In that case, the carrier base is low viscosity hydroxypropyl methylcellulose having a number average molecular weight below 50,000 and a hydroxypropoxyl content of 9–12%. Specifically cited as examples corresponding to these criteria are Methocel E50 and Metolose 60SH50, which are 50 cps viscosity grade hydroxypropyl methylcellulose having number average molecular weight in the range of 23,000. Examples 1–4 describe tablets consisting essentially of about 57% by weight of one or the other of these two materials in combination with lithium carbonate. The tablets weighed about 700 mg and released the active agent for up to 14 hours in vitro. Examples 5–6 describe sustained release aspirin tablets in which the hydroxypropyl methylcellulose carrier base constitutes 16.5% of the total weight of the tablet. The tablets had an average weight of 787 mg and released 650 mg aspirin in vitro over a period of 6–8 hours. Further examples in U.S. Pat. No. 4,369.172 show tablets containing 16–20% by weight of the polymer and release of the active ingredient over 1–6 hours in vitro.

The Dow Chemical Company publishes a brochure entitled "Formulating Sustained Release Pharmaceutical Products with Methocel" (1982) which describes the various commercially available Methocel polymers, identifying their relative viscosities, rates of hydration and gel strength properties. The brochure also suggests criteria for formulating sustained release pharmaceutical products.

While the concept of utilizing hydroxypropylmethylcellulose in oral dosage forms to prolong the rate of release of drugs into the blood stream is known, and prolonged release of various active agents from such dosage forms has been demonstrated, the art available to formulate oral controlled release forms of naproxen and naproxen sodium has several disadvantages. First, it is apparent from the foregoing discussion of the relevant art that presently known sustained release tablet formulations rely on fairly high levels of hydroxypropyl methylcellulose to achieve adequate duration of drug release. The major problem with using any of these formulations is the additional bulk of the resulting tablet. In dry oral dosage forms, there is an approximate upper limit to the tablet bulk that will be tolerated by the patient. This limit varies from patient to patient, but can be as low as 650 mg. Thus, with drugs such as naproxen, whose therapeutic dosage range is 500–1200 mg/day, the additional tablet bulk which is created by inclusion of substantial amounts of matrix material will render the tablets unacceptable to many patients.

Furthermore, while the art demonstrates in vitro sustained drug release from several formulations using hydroxypropyl methylcellulose, the pharmacokinetics of in vivo drug release, absorption, distribution, metabolism and excretion impose more demanding requirements on the design of the controlled release tablet formulation than are apparent from in vitro testing. The present invention is directed to a new controlled release oral dosage formulation for naproxen or naproxen sodium which provides sustained therapeutic plasma drug levels for at least 24 hours, and requires a surprisingly small amount, about 4–9 weight percent, of hydroxypropyl methylcellulose. The low level of matrix material required by the present invention makes possible a once-daily naproxen or naproxen sodium dosage form without excessive bulk, having weight and size characteristics which make it well-adapted for practical and acceptable patient administration. Chronic once-daily administration of the controlled release tablets of the present invention also provides less fluctuation in plasma drug concentration than is provided by chronic twice-daily administration of conventional naproxen and naproxen sodium tablets. Additionally, the new formulation is advantageous from a manufacturing viewpoint since it requires the presence of only three elements: the naproxen or naproxen sodium, the hydroxypropylmethylcellulose, and a lubricating agent.

SUMMARY OF THE INVENTION

The present invention is a controlled release tablet for once-daily oral administration of 500–1200 mg of naproxen or naproxen sodium which tablet comprises a homogeneous matrix comprising:

about 4–7 weight percent of hydroxypropylmethylcellulose having a number average molecular weight in the range of from about 80,000 to about 130,000, about 81–96 weight percent of naproxen or naproxen sodium in an amount effective for once daily oral administration, and about 0.1 to about 2 weight percent of a pharmaceutically acceptable lubricating agent.

Figure 1:
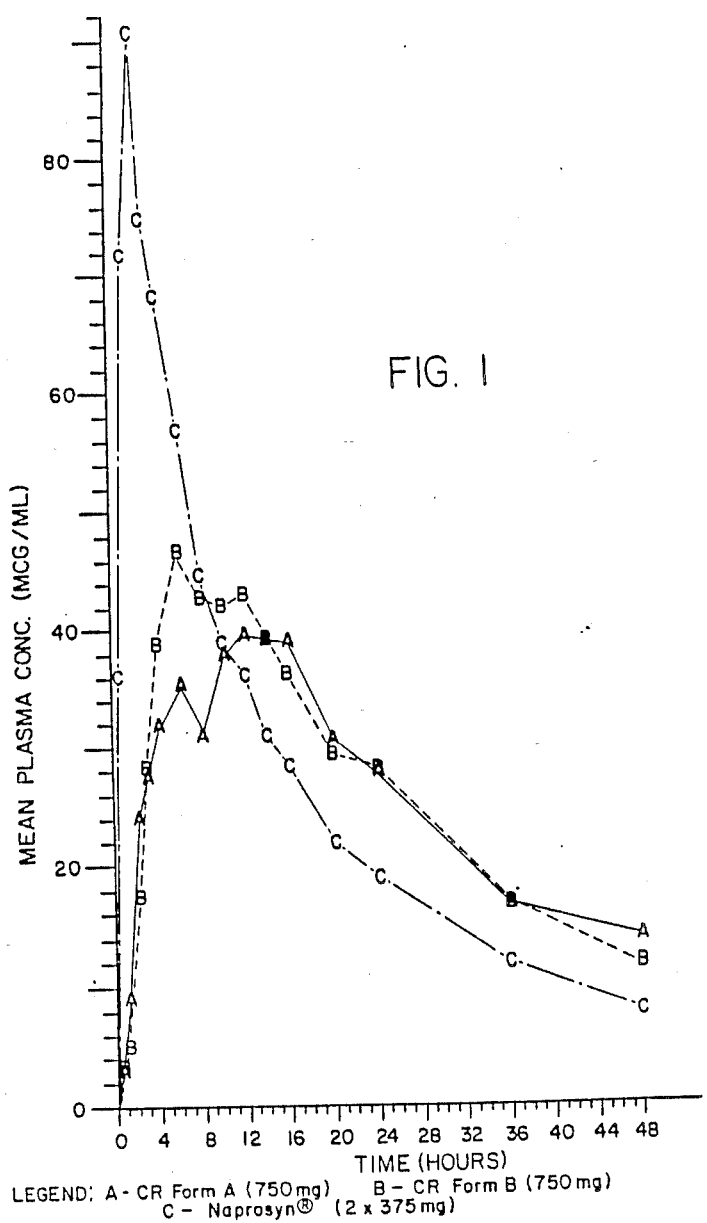
FIG. 1 is a graphical illustration of results of the test described in Example 3 showing comparative plasma levels of naproxen over a 48 hour period achieved by single doses of two different 750 mg controlled release formulations prepared according to the present invention, as described in Examples 1 and 2 (lines A and B) as compared with a single dose (2x375 mg tablets) of Naprosyn ® brand naproxen (line C).
Figure 2:
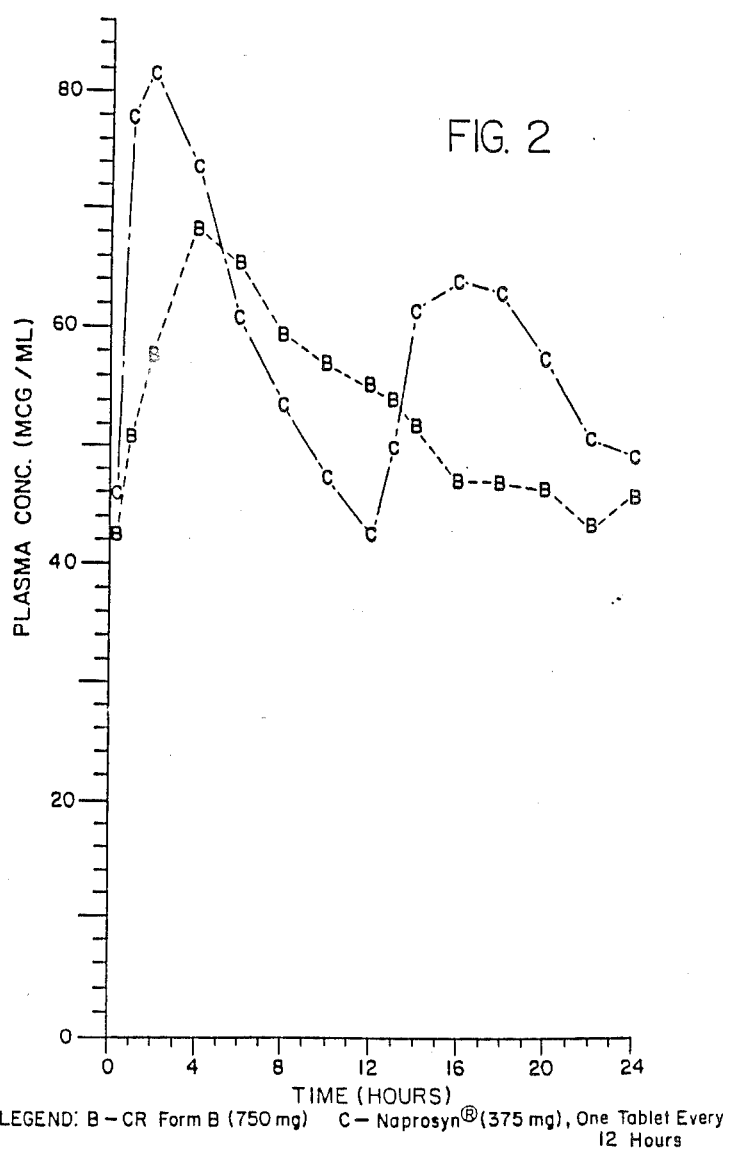
Figure 3:
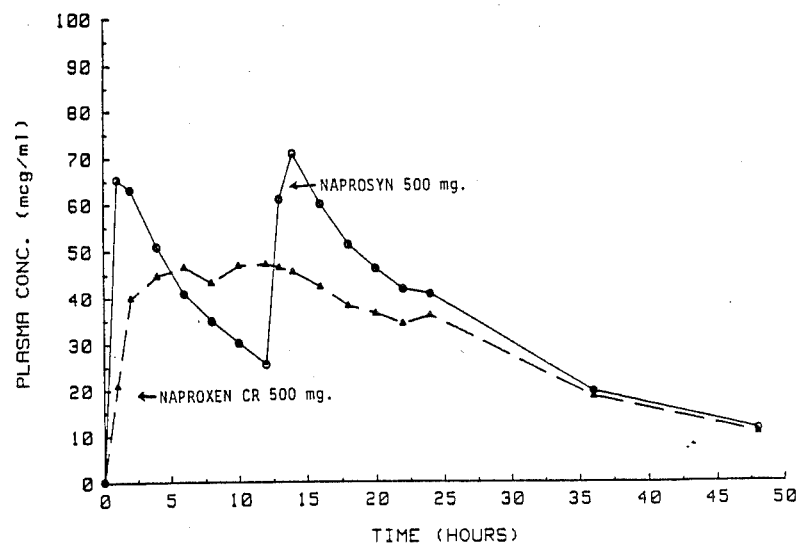

FIG. II is a graphical illustration of results of the test described in Example 5 showing comparative mean plasma concentrations of naproxen over a 24 hour period on day five of a multiple dose study. The mean plasma concentrations are steady state levels achieved by once-daily administration of the 750 mg controlled release formulation of the present invention (Formulation B, Example 2, line B of FIGURE II), or by once every 12 hour administration of Naprosyn ® brand naproxen, 375 mg (line C of FIGURE II).

FIGURE III is a graphical illustration of results of the test described in Example 3 showing comparative plasma levels of naproxen over a 48 hour period achieved by a single dose of two 500 mg controlled release tablets prepared according to the present invention as described in Example 7, compared with two consecutive single doses of Naprosyn ® brand naproxen, 500 mg, given every twelve hours.

DETAILED DESCRIPTION OF THE INVENTION

Accordingly, the present invention provides a new controlled release oral tablet for once daily administration of 500–1200 mg of naproxen or naproxen sodium, which tablet comprises a homogeneous matrix comprising:

about 4–7 weight percent of hydroxypropylmethylcellulose having a number average molecular weight in the range of from about 80,000 to about 130,000, about 81–96 weight percent of naproxen or naproxen sodium in an amount effective for once daily oral administration, and about 0.1 to about 2 weight percent of a pharmaceutically acceptable lubricating agent.

The tablet matrix includes a minor amount of a pharmaceutically acceptable lubricating agent such as magnesium stearate to aid in the tableting process. This amount will vary between about 0.1 and 2% generally, and preferably represents about 1% of the total weight of the tablet. Suitable tablet lubricants include magnesium stearate, stearic acid, calcium stearate and the like, or mixtures thereof. Magnesium stearate is preferred.

Optionally, the tablet matrix may include minor amounts of other pharmaceutically acceptable excipients such as colorants and glidants. Suitable colorants include, but are not limited to, FD & C Yellow #5, FD&C Yellow #6, and FD&C Blue #2, and generally represent 1% or less of the tablet weight. Suitable glidants include, but are not limited to, pharmaceutical grades of talc and fused silica, and generally represent 7% or less of the tablet weight.

The term matrix, as used herein, refers to a uniform mixture of naproxen, hydroxypropyl methylcellulose, a lubricating agent, and other optionally included excipients. An important aspect of the present invention is the fact that the hydroxypropyl methylcellulose is uniformly dispersed throughout the matrix to achieve uniform drug release. The matrix may be made by any pharmaceutically acceptable technique which achieves uniform blending, including dry blending, conventional wet granulation, compression granulation, and fluid-bed granulation. Tablets can be made from the resulting matrix by any known tableting technique.

In accordance with the present invention, the amount of naproxen or naproxen sodium that is incorporated in a tablet may range between about 500 and about 1200 mg. The therapeutic range of about 500–1100 mg per tablet is indicated for the treatment of pain of arthritis, dysmenorrhea and other conditions. The tablet of the present invention provides a release period suitable for once-daily dosing, i.e. once within a 24 hour period. Generally, naproxen and naproxen sodium are administered at levels of 500–550, 750–800 or 1000–1100 mg/day, depending on the physician's judgement of the needs of the patient. Naproxen is generally administered at levels of 500, 750 or 1000 mg/day, while naproxen sodium is generally administered at levels of 550 or 1100 mg/day.

The hydroxypropylmethylcellulose utilized in the present invention is a water soluble cellulose ether, and is commercially available in various grades under the tradenames mentioned above in the BACKGROUND OF THE INVENTION. The physicochemical properties of these polymers vary over a wide range. Preferred embodiments of this invention utilize premium grade polymers of a single viscosity type having number average molecular weights in the range of about 80,000–130,000. However, a mixture of two or more grades or viscosity types resulting in number average molecular weights in the range of about 80,000–130,000 can be used.

The number average molecular weight of the hydroxypropyl methylcellulose which is used in the tablet matrix substantially influences the release profile which is obtained. The number average molecular weight (Mn) is the sum of the individual molecular weights of a representative sample population of molecules divided by the number of molecules in that sample, and is calculated from the limiting osmotic pressure of the solvent as the concentration of the hydroxypropyl methylcellulose approaches zero. The hydroxypropyl methylcellulose must have a number average molecular weight in the range of from about 80,000 to about 130,000, preferably from about 120,000 to about 130,000. When the polymer has a number average molecular weight of 120,000–130,000, it constitutes preferably about 4–6 weight percent of a 750 to 1000 mg naproxen controlled release tablet, about 7 weight percent of a 500 to 750 mg naproxen controlled release tablet, or about 6–8 weight percent of a naproxen sodium controlled release tablet. A second prefered range of number average molecular weight of the hydroxypropyl methylcellulose is about 85,000 to about 95,000. When the polymer has a number average molecular within this range, it constitutes preferably about 7–9 weight percent of the controlled release naproxen or naproxen sodium tablet.

Hydroxypropyl methylcelluloses which have number average molecular weights in the range suitable for use in the tablet matrix are generally available as single viscosity type polymers. As used herein, the term "single viscosity type" refers to commercially available grades of hydroxypropylmethylcellulose whose commercial designations reflect their individual viscosity type. Examples of single viscosity type hydroxypropylmethylcelluloses which are suitable for use in the present invention include Methocel Premium K4M, A4M, E4M and F4M (Dow Chemical Co., U.S.A.) which are 4000 cps viscosity polymers having number average molecular weights in the range of 85,000–95,000, and Methocel K15M, a 15,000 cps viscosity polymer having a number average molecular weight in the range of 120,000–130,000. Other suitable polymers include Metolose SM, 60SH, 65SH, and 90SH, viscosity grades 4000, 8000, 15,000 and 30,000 available from Shin-Etsu Ltd., Japan. Specific preferred hydroxypropyl methylcelluloses are Methocel K4M Premium and Methocel K15M Premium.

Optionally, the controlled release tablets may be coated with any conventional or non-conventional coating which is pharmaceutically acceptable. Generally, the coatings will be applied for such purposes as product identification, printability of the tablet, light protection, aesthetic appearance and patient compliance, and will not effect the release rate profile of the tablet. Conventional coating formulations which may be used include aqueous and solvent-based polymeric, gum and cellulose-based films, as well as sugar coatings. Numerous pharmaceutically acceptable coating formulations have been developed by the pharmaceutical industry and are well known to the pharmaceutical scientist.

Exemplary of typical film coating materials are formulations of such film forming agents as polyvinylpyrrolidone, acrylic polymers and copolymers, natural gums and resins, low molecular weight hydroxypropyl methylcellulose, hydroxypropyl cellulose, ethyl cellulose and methylcellulose. These formulations may include plasticizing agents such as acetylated monoglycerin, castor oil, mineral oil, glycerol, diethyl phthalate, triethylcitrate, triacetin, glycerin, propylene glycol, polyethylene glycol, and the like, as well as surface active agents such as polysorbates, colorants, and opacifiers such as titanium dioxide and talc.

A preferred coating formulation for the tablets of this invention comprises a mixture of low molecular weight hydroxypropyl methylcellulose and polyethylene glycol. Such coatings are readily formulated by standard means well known to the pharmaceutical chemist, and are also commercially available. Exemplary of a commercially available coating material suitable for application to the tablets of this invention is Opadry ®, a low molecular weight hydroxypropyl methylcellulose/-polyethylene glycol material available from Colorcon.

The controlled release tablets of the present invention provide therapeutic blood levels of naproxen or naproxen sodium for at least 24 hours, and are thus suitable for once-daily administration. Fluctuations in blood levels during multi-dose therapeutic regimens are minimized by the tablets of the present invention, such that the ratio of mean peak plasma concentration to mean trough plasma concentration is 2:1 or lower.

The following examples serve to further illustrate the invention, but are not to be interpreted as limiting the scope of the appended claims in any way:

EXAMPLES 1 and 2

1. Sustained Release Naproxen Tablets, 750 mg (Formulation A)

Tablets were prepared from the following ingredients:

| Ingredients | grams | mg/tablet |
|---|---|---|
| 1 naproxen, USP | 3,555 | 750.0 |
| 2 hydroxypropylmethylcellulose, USP 2208, 15,000 cps (METHOCEL K15M Premium) | 356 | 75.1 |
| 3 magnesium stearate, NF | 40 | 8.4 |
| 4 deionized water, USP | 1,896 ml | * |
| TOTAL WEIGHT | | 0.83 grams/tablet |

2. Sustained Release Naproxen Tablets, 750 mg (Formulation B)

Tablets were prepared from the following ingredients:

| Ingredients | grams | mg/tablet |
|---|---|---|
| 1 naproxen, USP | 3,402 | 750.0 |
| 2 hydroxypropylmethylcellulose, 2208, 15,000 cps (METHOCEL K15M Premium) | 179 | 39.5 |
| 3 magnesium stearate, NF | 38 | 8.4 |
| 4 deionized water, USP | 1.004 | * |
| TOTAL WEIGHT | | 0.80 grams/tablet |

*Removed during processing.

Formulations A and B were prepared and made into tablets as follows: The naproxen and Methocel K15M were well blended, and then granulated with the purified water. The granulation was tray dried in a 50° C. oven for 16 hours, passed at slow speed through a hammer mill fitted with an 18 gauge screen, and then thoroughly mixed with the magnesium stearate. The resulting homogeneous matrix material was compressed into tablets of uniform weight and size. Tablets of Formulation A were compressed at 3000 pounds load, and tablets of Formulation B were compressed at 4000 pounds load.

EXAMPLE 3

A study was performed to determine the blood levels of naproxen after administration of single doses of controlled release Formulations A and B (Examples 1 and 2) over a 48 hour period using two Naprosyn ® 375 mg tablets, a non-controlled release form of naproxen, as the reference standard. Six healthy male volunteers, 21–35 years of age were selected for the study. The participants were not permitted to use hypnotics, sedatives, antihistamines or other enzyme-inducing drugs for a month prior to, or during the study. No drugs, including all over-the-counter drugs, or alcohol, were allowed 72 hours before or throughout the study period.

The study was performed as follows:

Following an overnight fast, single dose of the study drug formulations were administered to each participant at 8:00 a.m. on each of three days of dosing which were one week apart. The participants were randomized, and each participant received each formulation once. The study particpants continued to fast until the fourth hour blood sample has been obtained.

Ten milliliters of whole blood was collected in heparinized evacuated tubes on study days immediately before dosing and at 0.5, 1, 2, 3, 4, 6, 8, 10, 12, 14, 16, 20, 24, 36, and 48 hours post-dose. Plasma was separated and frozen for later assay of the naproxen plasma levels of HPLC. The resultant plasma levels determined for Formulations A and B and the standard Naprosyn ® tablet (Formulation C) are graphically depicted in FIG. I.

A similar study was performed which compared resulting plasma levels of naproxen following administration of a single dose of two uncoated 500 mg naproxen controlled release tablets described in Example 7 with the Naprosyn ® 500 mg tablet administered once every twelve hours (hours 0 and 12). The results are graphically depicted in FIG. III.

EXAMPLE 4

Controlled Release Naproxen Sodium Tablets, 550 mg

Tablets are prepared from the following ingredients:

| Ingredients | grams | mg/tablet |
|---|---|---|
| 1 naproxen sodium, USP | 5,500 | 550.0 |
| 2 hydroxypropylmethylcellulose, USP 2208, 15,000 cps (Methocel K15M Premium) | 412.5 | 41.25 |
| 3 talc, USP | 315 | 31.5 |
| 4 magnesium stearate, NF | 35 | 3.5 |
| 5 deionized water, USP | 2,100 | 36.0* |
| TOTAL WEIGHT | | 662.25 mg/tablet |

*remains as water of hydration for naproxen sodium

The naproxen sodium and Methocel K15M are well blended and then granulated with the purified deionized water. The granulation is tray dried in a 50° C. oven for 12 hours, passed at slow speed through a hammer mill which is fitted with an 18 mesh screen, and then thoroughly mixed with the talc and magnesium stearate. The resulting homogeneous matrix material is then pressed into tablets of uniform size and weight with 3500 pounds load compression.

EXAMPLE 5

A study was performed to determine the mean plasma levels of naproxen after multiple dosing of 750 mg controlled release naproxen tablets (Formulation B in EXAMPLE 2) administered once every 24 hours, and of Naprosyn ® brand naproxen (375 mg) tablets administered once every 12 hours. Twelve healthy male volunteers, 21-35 years of age were selected for the study. The participants were not permitted to use hypnotics, sedatives, antihistamines, or other enzyme-inducing drugs for a month prior to, or during, the study. No drugs, including all over-the-counter drugs, or alcohol, were allowed 72 hours before, or during, the study period.

The study was designed as a two-way crossover in which each subject received one of the study drugs over a five day period. Following an overnight fast, participants were administred one of the study drugs (either one 750 mg controlled release tablet of Formulation B, or one 375 mg Naprosyn ® brand tablet), at 9:00 a.m. according to a randomized schedule. At 9:00 p.m. those participants administered the reference product, Naprosyn ®, 375 mg, received their second dose of one Naprosyn ® tablet. The participants were maintained on a daily dose of the same study drug administered at the same time (or times) of the day for a total of 5 days.

Each day, immediately before the dose at 9:00 a.m., blood samples were drawn from each participant. Blood samples taken on the morning of the fifth day followed an overnight fast. Subsequent blood samples were taken at 1, 2, 4, 6, 8, 10, 12, 14, 16, 18, 20, 22, and 24 hours after the 9:00 a.m. dose on the fifth day. The samples were assayed for naproxen and the resulting mean plasma naproxen concentrations achieved by the controlled release tablets (line B) and the non-controlled release Naprosyn ® tablets (line C) are shown in FIG. II.

The results from this multiple dose study show that the naproxen bioavailability achieved by once-daily administration of the controlled release tablet (Formulation B) containing 750 mg of naproxen, is equivalent to that achieved by twice-daily administration of the Naprosyn ® 375 mg tablets. The ratio of mean peak plasma level to mean trough plasma level achieved by once-daily administration of Formulation B tablets was 1.6:1, whereas the peak to trough plasma level ratio achieved by administration of Naprosyn ® 375 mg tablets once every 12 hours was 1.9:1.

EXAMPLE 6

Controlled Release Naproxen Tablets, 500 mg (Colored)

Tablets were prepared from the following ingredients:

| Ingredients | grams | mg/tablet |
|---|---|---|
| 1 naproxen USP | 5000.0 | 500.0 |
| 2 hydroxypropylmethylcellulose, USP 2208, 15,000 cps (Methocel K15M Premium) | 380.7 | 38.07 |
| 3 magnesium stearate, NF | 54.4 | 5.44 |
| 4 FD & C Yellow No. 6 | 4.4 | 0.44 |
| 5 purified water, USP, sufficient for granulation | | * |
| TOTAL WEIGHT, uncoated | | 543.95 mg/tablet |
| coating suspension (optional): | | |
| 1 Opadry ® Clear YS-1-7006 | 108.8 | 10.88 |
| 2 purified water, USP | 1,087.9 | 108.79 |
| TOTAL WEIGHT, coated | | 663.62 mg/tablet |

*Removed during processing.

EXAMPLE 7

Controlled Release Naproxen Tablets, 500 mg (Uncolored)

Tablets were prepared from the following ingredients:

| Ingredients | grams | mg/tablet |
|---|---|---|
| 1 naproxen, USP | 5000.0 | 500.0 |
| 2 hydroxypropylmethylcellulose, USP 2208, 15,000 cps (Methocel K15M Premium) | 380.4 | 38.04 |
| 3 magnesium stearate, NF | 54.4 | 5.44 |
| 4 purified water, USP, sufficient for granulation | | * |
| TOTAL WEIGHT | | 543.48 mg/tablet |
| coating suspension (optional): | | |
| 1 Opadry ® Clear YS-1-7006 | 108.8 | 10.88 |
| 2 purified water, USP | 1,087.9 | 108.79 |

| -continued | | |
|---|---|---|
| Ingredients | grams | mg/tablet |
| TOTAL WEIGHT, coated | | 663.18 mg/tablet |

*Removed during processing.

The tablets described in Examples 6 and 7 were prepared and made into tablets as follows: The naproxen and Methocel K15M were well blended, and then granulated with the purified water, optionally containing dissolved FD&C Yellow #6. The granulations were tray dried in a 50° C. oven for 16 hours, passed at slow speed through a hammer mill fitted with an 18 gauge screen, and then thoroughly mixed with the magnesium stearate. The resulting homogeneous matrix material was compressed into tablets of uniform weight and size. Tablets were compressed at 3000 pounds load.

Some of the tablets were coated according to the following procedure: The Opadry ® was dissolved in approximately 80% of the water needed to make a 10% (wt/wt) solids solution, which was then passed through an 80 mesh screen, using the remaining water for quantitative transfer. The resulting suspension was sprayed onto the tablets where the tablets were coated and dried in a coating pan.

What is claimed is:

1. A controlled release tablet for once-daily oral administration of about 500–1200 mg of naproxen or naproxen sodium, which tablet comprises a homogeneous matrix comprising:
   about 4–7 weight percent of hydroxypropyl mehylcellulose having a number average molecular weight in the range of from about 80,000 to about 130,000,
   about 81–96 weight percent of naproxen or naproxen sodium in an amount effective for once daily oral administration, and
   about 0.1 to about 2 weight percent of a pharmaceutically acceptable lubricating agent.

2. The controlled release tablet of claim 1 which contains naproxen.

3. The controlled release tablet of claim 2 in which the amount of naproxen is about 500 mg, 750 mg or 1000 mg.

4. The controlled release tablet of claim 2 in which the hydroxypropyl methylcellulose has a number average molecular weight of about 120,000–130,000.

5. The controlled release tablet of claim 4 in which the hydroxypropyl methylcellulose constitutes about 4–6 weight percent of the matrix.

6. The controlled release tablet of claim 5 in which the matrix comprises:
   about 5 weight percent of the hydroxypropyl methylcellulose,
   about 85–95 weight percent naproxen, and
   about 0.1 to about 2 weight percent pharmaceutically acceptable lubricating agent.

7. The controlled release tablet of claim 6 wherein the amount of naproxen is about 500 mg, 750 mg or 1000 mg.

8. The controlled release tablet of claim 7 which includes a pharmaceutically accepable coating.

9. The controlled release tablet of claim 4 in which the matrix comprises:
   about 7 weight percent of the hydroxypropyl methylcellulose,
   about 82–93 weight percent naproxen or naproxen sodium, and
   0.1 to about 2 weight percent lubricating agent.

10. The controlled release tablet of claim 9 in which the amount of naproxen is about 500 mg, 750 mg or 1000 mg.

11. The controlled release tablet of claim 10 which includes a pharmaceutically acceptable coating.

12. The controlled release tablet of claim 4 in which comprises:
   (a) a matrix comprising
      about 5 weight percent of the hydroxypropyl methylcellulose,
      about 91–95 weight percent naproxen, and 0.1 to about 2 weight percent lubricating agent, and
   (b) a pharmaceutically acceptable coating.

13. The controlled release tablet of claim 12 which comprises:
   (a) a matrix comprising
      about 5 weight percent of the hydroxylpropyl methylcellulose,
      about 94 weight percent naproxen, and
      about 1 weight percent magnesium stearate, and
   (b) a pharmaceutically acceptable coating.

14. The controlled release tablet of claim 13 in which the amount of naproxen is about 500 mg, 750 mg, or 1000 mg.

15. The controlled release tablet of claim 4 which comprises:
   (a) a matrix comprising
      about 7 weight percent of the hydroxypropyl methylcellulose,
      about 89–93 weight percent naproxen, and 0.1 to about 2 weight percent lubricating agent, and
   (b) a pharmaceutically acceptable coating.

16. The controlled release tablet of claim 15 which comprises:
   (a) a matrix comprising
      about 7 weight percent of the hydroxypropyl methylcellulose,
      about 92 weight percent naproxen, and
      about 1 weight percent magnesium stearate, and
   (b) a pharmaceutically acceptable coating.

17. The controlled release tablet of claim 16 in which the amount of naproxen is about 500 mg, 750 mg, or 1000 mg.

* * * * *

UNITED STATES PATENT AND TRADEMARK OFFICE
CERTIFICATE OF CORRECTION

PATENT NO. : 4,803,079

DATED : February 7, 1989

INVENTOR(S) : Charles H. Hsiao et al

It is certified that error appears in the above-identified patent and that said Letters Patent is hereby corrected as shown below:

On the title page assignee should read

--(73) Assignee: Syntex Pharmaceuticals International Limited, Hamilton, Bermuda --.

Signed and Sealed this

Second Day of January, 1990

*Attest:*

JEFFREY M. SAMUELS

*Attesting Officer*     *Acting Commissioner of Patents and Trademarks*